United States Patent [19]
Girten et al.

[11] Patent Number: 5,741,774
[45] Date of Patent: Apr. 21, 1998

[54] USE OF A CYTOKINE REGULATORY AGENT TO TREAT RHEUMATOID ARTHRITIS

[75] Inventors: Beverly E. Girten, San Diego; Ronald R. Tuttle, Escondido, both of Calif.

[73] Assignee: Trega Biosciences, Inc., San Diego, Calif.

[21] Appl. No.: 722,279

[22] Filed: Sep. 27, 1996

Related U.S. Application Data

[63] Continuation-in-part of Ser. No. 336,473, Nov. 19, 1994, which is a continuation-in-part of Ser. No. 151,534, Nov. 12, 1993, Pat. No. 5,420,109.

[51] Int. Cl.$^6$ ............... A61K 38/00; C07K 5/00; C07K 7/00; C07K 17/00
[52] U.S. Cl. .................. 514/8; 514/16; 514/17; 514/18; 530/317; 530/322; 530/328; 530/329; 530/330
[58] Field of Search ................... 514/8, 16–18; 530/322, 328, 330

[56] References Cited

U.S. PATENT DOCUMENTS 5,420,109  5/1995  Suto et al. ................... 514/8
5,457,129  10/1995  Aggarwal et al. ............ 514/557

OTHER PUBLICATIONS

Arai et al. Cytokines:Coordinators of immune and inflammatory responses. Annu. Rev. Biochem. 59: 783–836 Jun. 1990.

Wooley et al., "Influence of a Recombinant Human Soluble Tumor Necrosis Factor Receptor FC Fusion Protein on Type II Collagen–Induced Arthritis in Mice," *J. Immunol.* 151:6602–6607 (1993).

Wooley et al., "The Effect of an Interleukin–1 Receptor Antagonist Protein on Type II Collagen–induced Arthritis and Antigen–induced Arthritis in Mice," *Arthr. Rheum.* 36:1305–1314 (1993).

*Primary Examiner*—Cecilia J. Tsang
*Assistant Examiner*—Michael Bolin

[57] ABSTRACT

The present invention relates to the use of a cytokine regulatory agent to reduce the severity of rheumatoid arthritis.

15 Claims, 2 Drawing Sheets

USE OF A CYTOKINE REGULATORY AGENT TO TREAT RHEUMATOID ARTHRITIS

This application is a continuation-in-part of U.S. Ser. No. 08/336,473, filed Nov. 9, 1994, which is a continuation-in-part of U.S. Ser. No. 08/151,534, filed Nov. 12, 1993, now U.S. Pat. No. 5,420,109, issued May 30, 1995, the entire contents of each of which is incorporated herein by reference.

BACKGROUND OF THE INVENTION

1. Field of the Invention

This invention relates generally to the fields of medicine and immunopathology and, more specifically, to methods of using a cytokine regulatory agent to reduce the severity of rheumatoid arthritis in an individual.

2. Background Information

Cytokines are a class of proteins produced by macrophages and monocytes in response to viral or bacterial infection and in response to T cell stimulation during an immune response. Cytokines are normally present in very low concentrations in a tissue and mediate their effects through binding to high affinity receptors on specific cell types.

Various cytokines such as the interleukins (IL), interferons (IF) and tumor necrosis factors (TNF) are produced during immune and inflammatory responses and control various aspects of these responses. Following induction of an immune or inflammatory response, the concentrations of the various cytokines increase at different times. For example, following exposure of a subject to bacterial endotoxin, TNF and interleukin-6 (IL-6) levels increase, followed a few hours later by increases in the levels of IL-1 and IL-8

The cytokines, including TNF, IL-1, IL-2, IL-6 and IL-8, mediate host defense responses, cell regulation and cell differentiation. These cytokines can induce fever in a subject, cause activation of T and B cells and affect the levels of other cytokines, which result in a cascade effect whereby other cytokines mediate the biological action of the first cytokine.

The activation of these and other cytokines is responsible for the tissue damage and pain that occurs in various inflammatory conditions including pathoimmunogenic diseases such as rheumatoid arthritis. In a patient suffering from rheumatoid arthritis, levels of TNF, IL-1, IL-6 and IL-8 increase dramatically and can be detected in the synovial fluid. The cytokine cascade induced by expression of these cytokines further results in depressed lipoprotein metabolism as well as bone and cartilage destruction.

Cytokines have multiple biological activities and interact with more than one cell type. In addition, some cells interact with more than one type of cytokine. As a result, it has not been possible to prevent damage to healthy tissue by targeting one particular cytokine or cell type. For example, individual cytokine receptors or receptor antagonists that were designed to eliminate the biological effect due to one cytokine did not decrease mortality due to endotoxic shock, which is mediated by TNF, IL-1, IL-6 and IL-8.

A better approach for preventing tissue damage due to cytokines would be to regulate the expression of all or several of the cytokines involved in the response, without eliminating expression of any cytokine in its entirety. In this way, undesirable side effects such as complete immunosuppression can be prevented and homeostasis can be maintained.

Corticosteroids effectively modulate cytokine expression and are used to alleviate the clinical signs and symptoms associated with rheumatoid arthritis. However, corticosteroids can cause complete immunosuppression and have other undesirable side effects such as inducing "wasting" syndrome, diabetes and osteoporosis. Anti-inflammatory agents such as aspirin and non-steroidal anti-inflammatory drugs such as ketorolac (Toradol®; Syntex) also are effective in treating inflammation and pain. However, these drugs act by inhibiting prostaglandin production, which can lead to potentially severe complications including gastric ulceration, bleeding and renal failure.

In order to reduce the severity of rheumatoid arthritis due to the expression of cytokines, it would be advantageous if the levels of cytokines that contribute to the deleterious effects associated with rheumatoid arthritis could be regulated. For example, TNF is believed to have a role in rheumatoid arthritis and administration of a soluble TNF receptor fused to an immunoglobulin Fc domain resulted delayed the onset of an experimentally induced arthritis and resulted in a less severe grade of arthritis in mice. This result suggests that such a fusion protein could be useful for reducing the severity of rheumatoid arthritis.

Unfortunately, a biological material such as a TNF receptor/Fc domain fusion protein can be expensive to prepare in a form that is sufficiently pure for use as a therapeutic agent. In addition, such a fusion protein can present "foreign" epitopes that may induce an undesirable immune response in the treated subject. Such an immune response can decrease the effective concentration of the agent in the treated subject by binding to the fusion protein and can be involved in the formation of immune complexes, which can have deleterious effects in the treated subject. Thus, a need exists for a cost effective method of treating an individual suffering from rheumatoid arthritis, preferably using an agent that does not produce undesirable side effects in the treated patient. The present invention satisfies this need and provides related advantages as well.

SUMMARY OF THE INVENTION

The present invention relates to the use of a cytokine regulatory agent to reduce the severity of rheumatoid arthritis. Administration of a cytokine regulatory agent, which has the structure $X_1$—$X_2$—His—(D)Phe—Arg—(D)Trp—$X_3$ or $X_4$—$X_5$—(D)Phe—Arg—(D)Trp—$X_3$, where $X_1$, $X_2$, $X_3$, $X_4$ and $X_5$, when present, are amino acids or amino acid analogs, or modified forms of such structures, can reduce the onset or progression of rheumatoid arthritis in an individual.

DETAILED DESCRIPTION OF THE INVENTION

Figure 1:
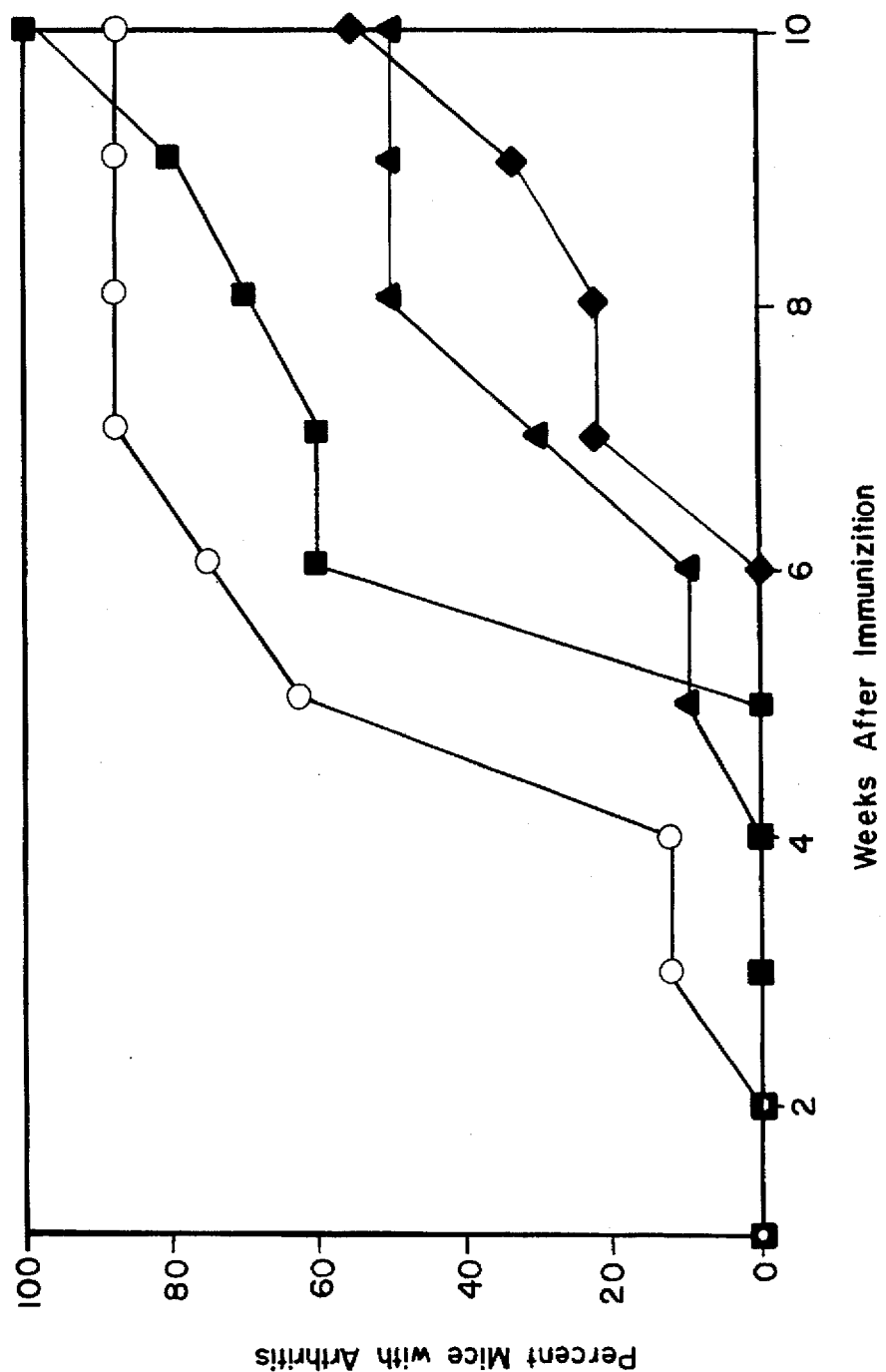
FIG. 1 shows the effect of treatment with various doses of CRA-2 on the time of onset of collagen induced arthritis in mice. Open circles indicate controls (saline treated); closed squares indicate 3 µg CRA-2; closed triangles indicate 30 µg CRA-2; and closed diamonds indicate 300 µg CRA-2.

The present invention provides a method of using a cytokine regulatory agent (CRA) to reduce the severity of rheumatoid arthritis in an individual that has or is susceptible to this patho-immunogenic disease. CRA's are known in the art and described, for example, in U.S. Pat. No. 5,420,109; issued May 30, 1995, which is incorporated herein by reference (CRA's previously were known as "cytokine restraining agents").

As disclosed herein, administration of a CRA can reduce the severity of rheumatoid arthritis in an individual that is susceptible to the disease. As used herein, the term "reduce the severity," when used in reference to the effect of a CRA on rheumatoid arthritis, means that the onset of the disease is delayed in an individual susceptible to developing the disease or that the progression of the disease is delayed in an individual suffering from rheumatoid arthritis.

Rheumatoid arthritis is a systemic, chronic, inflammatory disease that bilaterally affects joints, particularly elbows, knees, ankles ad spine (see Rubin and Farber, "Pathology" 2d ed. (J. B. Lippincott Co. 1994)). Although rheumatoid arthritis can occur at any age, onset of the disease generally occurs in the third or fourth decade and the prevalence increases until 70 years of age. The disease occurs in 1–2% of adults and affects women three times as frequently as men.

The onset of rheumatoid arthritis can be acute or can be slowly progressing. Generalized symptoms include slowly developing fatigue, weight loss, weakness and vague musculoskeletal discomfort, which ultimately localizes to the involved joints. As the disease progresses, joint surfaces are destroyed. About one fourth of the patients appear to recover completely from the disease, another one fourth of the patients have only slight functional impairment that can last for years, and about one half of the patients have a progressive disease that becomes disabling and can result in death (Ruben and Farber, supra, 1994).

A genetic contribution to the disease is indicated by the observation that rheumatoid arthritis occurs with increased frequency in first degree relatives of affected persons and occurs with 30% concordance in monozygotic twins. In addition, there is a significant association between development of rheumatoid arthritis and the HLA-Dw4 haplotype and a related B cell alloantigen, HLA-DRw4 (Ruben and Farber, supra, 1994).

Up to 80% of patients with classic rheumatoid arthritis are positive for rheumatoid factor, which represents anti-idiotypic antibodies against the Fc fragment of IgG. Although rheumatoid factor is not diagnostic of the disease, since it also can be found in patients having related collagen vascular diseases as well as other disorders, high titers of rheumatoid factor are associated with severe and unremitting disease, including systemic complications (Ruben and Farber, supra, 1994).

Prior to the present invention, drugs for treating rheumatoid arthritis included anti-inflammatory agents such as aspirin and corticosteroids; remission-inducing drugs such as gold salts and antimalarial drugs; and, in patients with severe, nonresponsive, progressive disease, immunosuppressive drugs such as cyclophosphamide and methotrexate. As disclosed herein, administration of a CRA such as Ac—Nle—Gln—His—(D)Phe—Arg—(D)TrP—Gly—NH$_2$ ("CRA-1") or Ac—His—(D)Phe—Arg—(D)Trp—Gly—NH$_2$ ("CRA-2") can reduce the severity of rheumatoid arthritis in an individual by delaying the onset or progression of the disease (see FIG. 1 and 2).

It should be recognized that, while a CRA is referred to as a cytokine regulatory agent and administration of a CRA to an individual susceptible to rheumatoid arthritis was associated with decreased levels of TNFα or IL-6 in the treated individual, no mechanism of action is proposed herein for the effectiveness of a CRA in reducing the severity of rheumatoid arthritis. Thus, a CRA may reduce the severity of rheumatoid arthritis by regulating cytokine activity or by some other mechanism that can be unrelated to cytokines.

The effectiveness of a CRA in reducing the severity of rheumatoid arthritis was demonstrated using the mouse model system of collagen-induced arthritis (CIA; Wooley et al., *J. Exp. Med.* 154:688–700 (1981); Wooley and Chapdelaine, *CRC Crit. Rev. Immunol.* 8:1 (1987); Wooley et al., *Arthr. Rheum.* 36:1305–1314 (1993a); Wooley et al., *J. Immunol.* 151:6602–6607 (1993b), each of which is incorporated herein by reference). The CIA mouse model utilizes the intradermal injection of type II collagen into mice to induce an arthritogenic reaction that is characteristic of the reaction that occurs in a patient with rheumatoid arthritis. Following injection of mice in the back with native chick type II collagen in Freund's complete adjuvant, swelling and erythema initially appears in one or more paws and progresses such that increased paw thickness occurs, followed by gross joint deformation and loss of joint mobility. About 50% of the injected animals in susceptible strains show evidence of disease and the histopathologic, immunologic and genetic features of CIA in mice correspond to those observed in rheumatoid arthritis (see Wooley et al., supra, 1981; 1993b).

Figure 2:
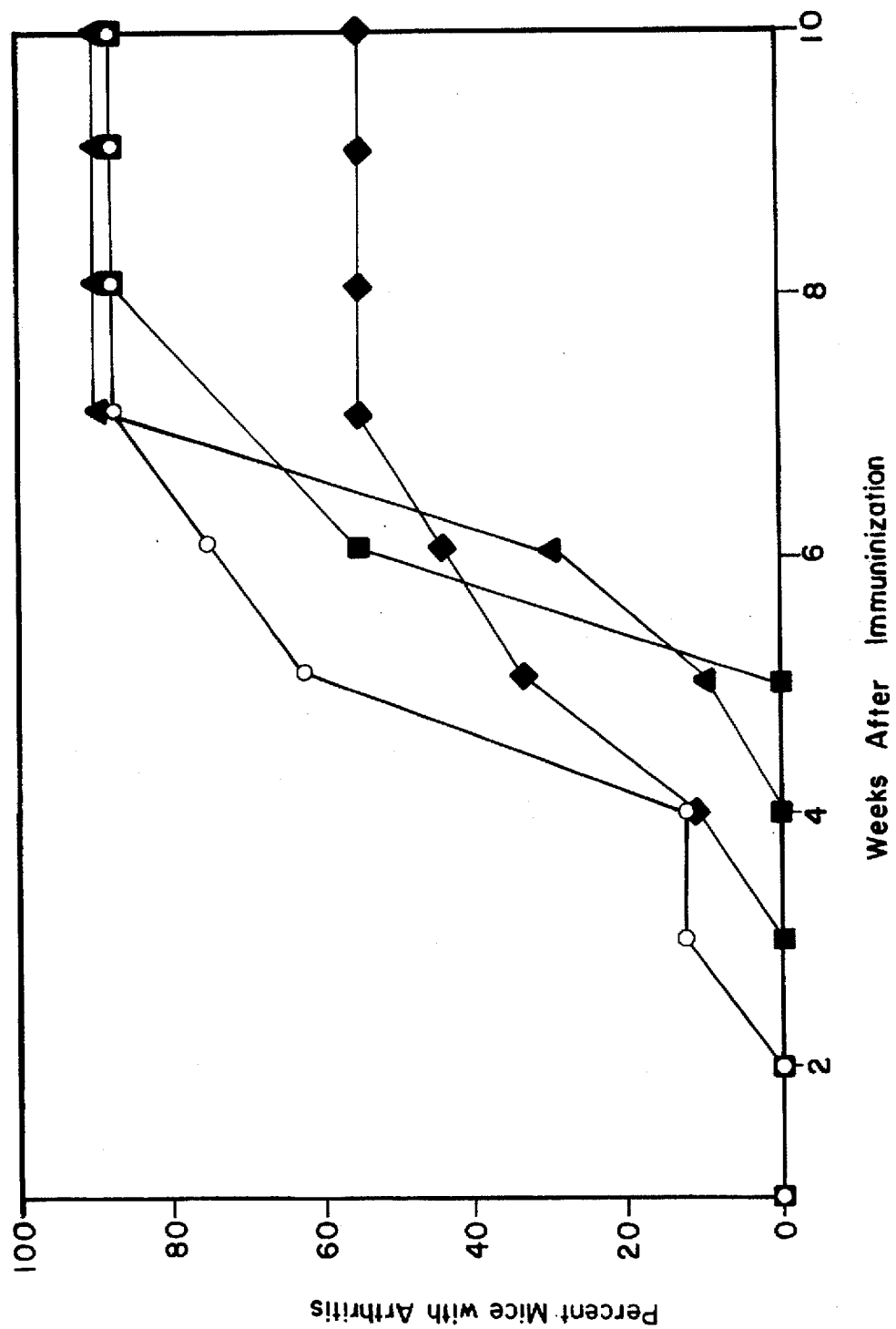
FIG. 2 shows the effect of treatment with various doses of CRA-1 on the time of onset of collagen induced arthritis in mice. Open circles indicate controls (saline treated); closed squares indicate 3 µg CRA-1; closed triangles indicate 30 µg CRA-1; and closed diamonds indicate 300 µg CRA-1.

As exemplified herein, administration of a CRA such as CRA-1 or CRA-2 delayed the onset of CIA in mice (see Example II and FIGS. 1 and 2). In addition, administration of 300 μg CRA-2 significantly reduced the progression of CIA from the inflammatory phase to the deforming phase as compared to that in untreated control animals. These results indicate that administration of a CRA can reduce the severity of CIA in mice and further indicate that a CRA can be effective in reducing the severity of rheumatoid arthritis in an individual.

Since CRA's are known to regulate cytokine levels and because a role for cytokines is suggested in rheumatoid arthritis, the levels of IL-1, IL-2, IL-6 and TNFα were determined in the CIA studies (see Example II). A dose dependent decrease in IL-6 levels in mice treated with CRA-2 correlated with the dose dependent delayed onset and progression of CIA (FIG. 1). In comparison, a significant decrease in TNFα levels was observed in mice that were treated with CRA-1, although the magnitude of the decrease in TNFα levels did not correlate with the moderate delay in onset of the disease. These results indicate that different CRA's, which can effectively reduce the severity of CIA, variously regulate the expression of different cytokines. Thus, while the reduction in IL-6 levels correlated with the reduction in the severity of CIA in mice treated with CRA-2, indicating that regulation of IL-6 levels by CRA-2 is involved in the clinical effect, such a potential mechanism was not readily apparent in mice treated with CRA-1. It should be recognized, however, that the effect of CRA-1 may correlate with the regulation of a cytokine such as an interferon, the expression of which was not examined in these studies.

The present invention was exemplified using CRA-1 and CRA-2 (see Example I). In general, however, a CRA useful for reducing the severity of rheumatoid arthritis in an individual has the structure:

X$_1$—X$_2$—His—(D)Phe—Arg—(D)Trp—X$_3$, where $X_1$ is

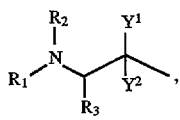

H or $COCH_3$;

$X_2$ is

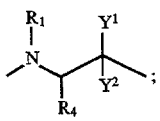

and $X_3$ is

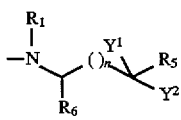

or $R_5$;

where $Y^1$ and $Y^2$ are independently a hydrogen atom, or are taken together to form a carbonyl or thiocarbonyl; $R_1$ is H, $COCH_3$, $C_2H_5$, $CH_2Ph$, COPh, COO-t-butyl, $COOCH_2Ph$, $CH_2CO$—(polyethylene glycol) or A; $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$—$CON_2$, $(CH_2)_m$—$CONHR_1$ or $(CH_2)_m$—CONHA; $R_5$ is OH, $OR_3$, $NH_2$, SH, $NHCH_3$, $NHCH_2Ph$ or A; and $R_6$ is H or $R_3$;

and where "Ph" is $C_6H_5$, "m" is 1, 2 or 3, "n" is 0, 1, 2 or 3, and "A" is a carbohydrate having the general formula:

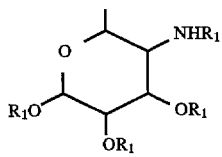

(U.S. Pat. No. 5,420,109; supra, 1995).

In addition, a CRA useful in the invention can have the structure:

$X_4$—$X_5$—(D)Phe—Arg—(D)Trp—$X_3$, where $X_4$ is

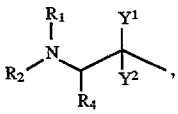

H, $COCH_3$ or absent;

$X_5$ is His, H or $COCH_3$; and $X_3$ is

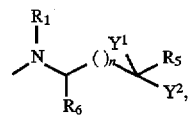

$NH_2$ or OH;

where $Y^1$ and $Y^2$ are independently a hydrogen atom, or are taken together to form a carbonyl or thiocarbonyl; $R_1$ is H, $COCH_3$, $C_2H_5$, $CH_2Ph$, COPh, COO-t-butyl, $COOCH_2Ph$, $CH_2CO$—(polyethylene glycol) or A; $R_2$ is H or $COCH_3$; $R_4$ is $(CH_2)_m$—$CONH_2$, $(CH_2)_m$—$CONHR_1$ or $(CH_2)_m$—CONHA; $R_5$ is OH, $OR_3$, $NH_2$, SH, $NHCH_3$, $NHCH_2Ph$ or A; and $R_6$ is H or $R_3$;

and where "Ph" is $C_6H_5$, "m" is 1, 2 or 3, "n" is 0, 1, 2 or 3, and "A" is a carbohydrate having the general formula

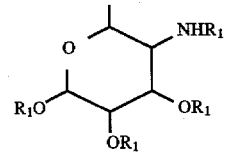

(see U.S. Pat. No. 5,420,109, supra, 1995, which also discloses methods for making a CRA).

In general, a CRA is a peptide or a peptide-like structure such as a peptidomimetic or a peptoid (see Ecker and Crooke, *Biotechnology* 13:351–360 (1995), and Blondelle et al., *Trends Anal. Chem,* 14:83–92 (1995), and the references cited therein, each of which is incorporated herein by reference). Amino acids are indicated herein by their commonly known three letter code, where "(D)" designates an amino acid having the "D" configuration, as compared to the naturally occurring (L)-amino acids; "Nle" is the three letter code for norleucine. Where no specific configuration is indicated, one skilled in the art would understand the amino acid to be an (L)-amino acid. In the CRA structures shown above, "Ph" indicates a "phenyl" group ($C_6H_5$). CRA peptides are written in the conventional manner, such that the amino-terminus (N-terminus) is shown to the left and the carboxy-terminus (C-terminus) is shown to the right.

One skilled in the art would know that the choice of amino acids or amino acid analogs incorporated into the peptide will depend, in part, on the specific physical, chemical or biological characteristics required of the CRA. Such characteristics are determined, for example, by the route by which the CRA is administered.

Selective modification of a reactive group in a peptide also can impart desirable characteristics to a CRA. For example, the N-terminus can be modified by acetylation or the C-terminus can be modified by amidation. Methods for modifying the N-terminus or C-terminus of a peptide are well known in the art (see, for example, in U.S. Pat. No. 5,420,109, supra, 1995). The choice of modifications made to the reactive groups present on the peptide is determined by a desirable characteristic required in the CRA. A CRA having the structure Ac—Nle—Gln—His—(D)Phe—Arg—(D)Trp—Gly—$NH_2$ (CRA-1) or the structure Ac—His—(D)Phe—Arg—(D)Trp—Gly—$NH_2$ (CRA-2) is an example of a CRA that is modified both by acetylation at the N-terminus and by amidation at the C-terminus.

A cyclic peptide also can be an effective CRA. A cyclic peptide can be obtained by inducing the formation of a covalent bond between, for example, the amino group at the N-terminus of the peptide and the carboxyl group at the C-terminus. For example, the peptide, cyclo(His—(D)Phe—Arg—(D)Trp), can be produced by inducing the formation of a covalent bond between His and (D)Trp. Alternatively, a cyclic peptide can be obtained by forming a covalent bond between a terminal reactive group and a reactive amino acid side chain or between two reactive amino acid side chains such as the sulfhydryl reactive groups present in cysteine residues. One skilled in the art would know that the choice of a particular cyclic peptide is determined by the reactive groups present on the peptide as well as the desired characteristic of the peptide. Cyclization of a CRA peptide can provide the CRA with increased stability in vivo.

In addition to the examples provided above, other representative cytokine regulatory agents include:
1) Ac—Nle—Gln—His—(D)Phe—Arg—(D)Trp—Gly—OH;
2) Ac—Nle—Gln—His—(D)Phe—Arg—(D)Trp—Gly—OC$_2$H$_5$;
3) Ac—Nle—Gln—His—(D)Phe—Arg—(D)Trp—Gly—NH—NH$_2$;
4) Ac—Nle—Asn—His—(D)Phe—Arg—(D)Trp—Gly—NH$_2$;
5) Ac—Nle—Asn—His—(D)Phe—Arg—(D)Trp—Gly—OH;
6) Ac—Nle—Gln—His—(D)Phe—Arg—(D)Trp—Gly—NHCH$_2$CH$_2$Ph;
7) Ac—Nle—Gln—His—(D)Phe—Arg—(D)Trp—Gly—NHCH$_2$Ph;
8)

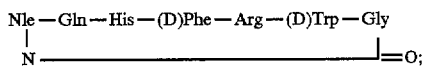

9) Ac—Gln—His—(D)Phe—Arg—(D)Trp—Gly—NH$_2$;
10) Ac—Nle—Gln—His—(D)Phe—Arg—(D)Trp—N$_2$;
11) His—(D)Phe—Arg—(D)Trp—NH$_2$;
12) Ac—His—(D)Phe—Arg—(D)Trp—OH; and
13) Ac—His—(D)Phe—Arg—(D)Trp—(CH$_2$NHAc)—Gly—NH$_2$, where "—(CH$_2$NHAc)—" indicates a modified peptide bond between (D)Trp and Gly.

Peptide cytokine regulatory agents as described above are characterized, in part, by a core structure (D)Phe—Arg—(D)Trp, where the amino acids are indicated by their commonly known three letter code and where "(D)" designates an amino acid having the "D" configuration, as opposed to the naturally occurring L-amino acids. Where no specific configuration is indicated, one skilled in the art would understand the amino acid to be an (L)-amino acid. In the peptides exemplified above, "Nle" is the three letter code for norleucine and "Ph" indicates a "phenyl" group (C$_6$H$_5$).

Cytokine regulatory agents are synthesized using a modification of the solid phase peptide synthesis method of Merrifield (J. Am. Chem. Soc., 85:2149 (1964), which is incorporated herein by reference; see Example I) or can be synthesized using standard solution methods well known in the art (see, for example, Bodanszky, M., *Principles of Peptide Synthesis* 2nd revised ed. (Springer-Verlag, 1988 and 1993), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

Peptides were synthesized using amino acids or amino acid analogs, the active groups of which were protected as required using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenyl acetamido methyl and 4-(hydroxymethyl)phenoxymethylcopoly(styrene-1% divinylbenzene) (Wang resin), all of which are commercially available, or to p-nitro benzophenone oxime polymer (oxime resin), which can be synthesized as described by De Grado and Kaiser, *J. Org. Chem.* 47:3258 (1982), which is incorporated herein by reference (see Example I).

One skilled in the art would know that the choice of amino acids or amino acid analogs incorporated into the peptide will depend, in part, on the specific physical, chemical or biological characteristics required of the cytokine regulatory peptide. Such characteristics are determined, in part, by the route by which the cytokine regulatory agent will be administered or the location in a subject to which the cytokine regulatory agent will be directed.

With regard to selective modification of the reactive groups in a peptide, the peptides can be manipulated while still attached to the resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or methods for amidation of the C-terminus. Similarly, methods for modifying side chains of the amino acids or amino acid analogs are well known to those skilled in the art of peptide synthesis. The choice of modifications made to the reactive groups present on the peptide will be determined by the characteristics that the skilled artisan requires in the peptide.

A newly synthesized peptide can be purified using a method such as reverse phase high performance liquid chromatography (RP-HPLC; see Example I) or other methods of separation based on the size or charge of the peptide. Furthermore, the purified peptide can be characterized using these and other well known methods such as amino acid analysis and mass spectrometry (see Example I).

A CRA generally is administered to an individual as a pharmaceutical composition comprising a cytokine regulatory agent and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the cytokine regulatory agent or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the cytokine regulatory agent and on the particular physico-chemical characteristics of the specific cytokine regulatory agent.

The present invention provides a method of reducing the severity of rheumatoid arthritis in an individual by administering a CRA to the individual. One skilled in the art would know that a pharmaceutical composition comprising a cytokine regulatory agent can be administered to a subject having pathologically elevated cytokine activity by various routes including, for example, orally or parenterally, such as intravenously, intramuscularly, subcutaneously, intraorbitally, intracapsularly, intraperitoneally, intracisternally, intra-articularly or by passive or facilitated absorption through the skin using, for example, a skin patch or transdermal iontophoresis, respectively. Thus, a CRA can be administered by injection, intubation, orally or topically, the latter of which can be passive, for example, by direct application of an ointment or powder, or active, for example, using a nasal spray or inhalant.

A CRA also can be administered as a topical spray, in which case one component of the composition is an appropriate propellant. Thus, where the CRA is in a composition that can be absorbed through the skin, topical administration of the CRA in the region of a joint affected by rheumatoid arthritis can be particularly useful. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer. Since cytokine levels in an individual with rheumatoid arthritis are elevated locally in the affected joints as well as systemically, one skilled in the art would recognize that a CRA can be administered directly in the region of an affected joint or can be administered intravenously or can be suspended or dissolved in an appropriate pharmaceutically acceptable carrier and administered, for example, into the lungs using a nasal spray.

In order to reduce the severity of rheumatoid arthritis in an individual, a CRA must be administered in an effective dose, which is about 0.01 to 100 mg/kg body weight per administration. The total treatment dose can be administered to a subject as a single dose, either as a bolus or by infusion over a relatively short period of time, or can be administered using a fractionated treatment protocol, in which the multiple doses are administered over a more prolonged period of time. One skilled in the art would know that the amount of a cytokine regulatory agent required to obtain an effective dose in a subject depends on many factors including the age and general health of the subject as well as the route of administration and the number of treatments to be administered. In view of these factors, the skilled artisan would adjust the particular dose so as to obtain an effective dose for regulating cytokine activity.

A CRA can be administered to an individual prior to the onset of the disease, in which case administration of the CRA can reduce the severity of rheumatoid arthritis by delaying onset. Such a preventive administration preferably is used in an individual that exhibits genetic factors indicating a predisposed susceptibility to the disease. Thus, an individual having an HLA-Dw4 haplotype or expressing and a related B cell alloantigen, HLA-DRw4, can be predisposed to developing rheumatoid arthritis and, therefore, is a candidate for preventive treatment. In particular, such an individual is a candidate for preventive treatment if rheumatoid arthritis occurs in family members of the individual. Based on the individual's family history, the skilled artisan can determine when such a preventive treatment should be initiated.

Administration of a CRA also can be useful for treating an individual suffering from rheumatoid arthritis. Preferably, treatment is initiated in the initial stages of the disease such that morbidity due to the disease is minimized. Administration of a CRA to an individual suffering from rheumatoid arthritis provides the substantial advantage that progression of the disease can be delayed, thereby reducing the severity of the disease. In an individual suffering from more a more severe stage of rheumatoid arthritis, administration of a CRA can be particularly useful when administered in combination, for example, with a conventional agent such as an anti-inflammatory agent or a remission-inducing agent (see Rubin and Farber, supra, 1994). The skilled artisan would administer a CRA, alone or in combination with a second agent, based on the clinical signs and symptoms exhibited by the individual and would monitor the effectiveness of such treatment using routine methods such as radiologic, immunologic and, where indicated, histopathologic methods.

The following examples are intended to illustrate but not limit the invention.

EXAMPLE I

SYNTHESIS OF CRA-1 AND CRA-2

This example describes methods for the solid phase synthesis of peptide cytokine regulatory agents.

Cytokine regulatory agents having the amino acid sequences Ac—Nle—Gln—His—(D)phe—Arg—(D)Trp—Gly—$NH_2$ (CRA-1; heptapeptide) and Ac—His—(D)Phe—Arg—(D)Trp—Gly—$NH_2$ (CRA-2; pentapeptide) were synthesized using a modification of the solid phase peptide synthesis method of Merrifield (1964). Essentially, MBHA resin containing a t-BOC glycine derivative (Advanced Chemtech; Louisville, Ky.) was added to a reaction vessel suitable for solid phase peptide synthesis (see Houghten, 1985). The resin was washed three times with methylene chloride and the t-BOC protecting group was removed using trifluoroacetic acid (TFA) containing 1–2% anisole in methylene chloride. The resin then was washed with methylene chloride and treated with diisopropylethylamine.

The peptide was extended by the addition of 3.2 equivalents of N-formyl-BOC-protected D-tryptophan in dimethylformamide and 3.0 equivalents of dicyclohexylcarbodiimide. The reaction was monitored using ninhydrin and was allowed to proceed for 25 min, after which the resin was washed using methylene chloride. The procedure was repeated using di-tolulyl-BOC arginine, then with each of the desired protected amino acids until the appropriate pentapeptide or heptapeptide was synthesized.

The amino terminus of each peptide was acetylated by treating the sample with acetic anhydride, diisopropylethylamine and methylene chloride for 2 hr. Following synthesis of the peptides, the N-formyl protecting group on the tryptophan residue was removed using 20% piperidine in DMF and the resin was washed with methylene chloride. The peptide was cleaved from the resin using anhydrous hydrogen fluoride (HF) containing 10% anisole, the reaction mixture was concentrated and the residue was digested with aqueous acetic acid. The acetic acid fraction, which contained the digested sample, was removed and the residue was washed with water. The wash was added to the acetic acid fraction and the combined sample was concentrated.

Each of the resulting crude peptides was purified by RP-HPLC (Vydac, C-18 column, using a gradient of 1 to 60% solution B over 30 min (solution A is 0.1% TFA/water and solution B is 0.1% TFA/acetonitrile). The acetylated heptapeptide (CRA-1) was determined to be 98% pure by RP-HPLC (Vydac C-18 column, using isocratic 24% solution B; absorption determined at 215 nm). The mass of each purified peptide was determined by plasma absorption mass spectrometry using a BioIon 20 Mass Analyzer time of flight detector. The mass was measured to be 985.2 daltons, which was same as the expected molecular mass. The acetylated pentapeptide (CRA-2) had a measured mass of 743 daltons and was greater than 97% pure.

EXAMPLE II

ADMINISTRATION OF A CRA REDUCES THE SEVERITY OF RHEUMATOID ARTHRITIS

This example describes the effectiveness of the cytokine regulatory agents, CRA-1 and CRA-2, for reducing severity of a collagen-induced arthritis (CIA) in experimental animals.

DBA/1 mice (8 weeks old; Jackson Laboratories; Bar Harbor Me.) were obtained and quarantined for 3 weeks prior to initiating these studies. Groups of 10 mice each were assigned to seven groups and were treated as follows: 1) 100 μl sterile saline (controls); 2) 100 μl 300 μg CRA-1 (in vehicle); 3) 100 μl 30 μg CRA-1; 4) 100 μl 3 μg CRA-1; 5) 100 μl 300 μg CRA-2; 6) 100 μl 30 μg CRA-2; and 7) 100 μl 3 μg CRA-2. The treatments were administered intraperitoneally 2×/day, 7 days/week, for ten weeks, when the study was terminated.

Three days after initiating treatment, the mice were injected intradermally at the base of the tail with 100 μg bovine type II collagen in Freund's complete adjuvant. Mice were monitored by daily for the onset of disease. In addition, blood samples were obtained from each mouse prior to initiating the study ("pretreatment sample"), at two and four weeks post-immunization, and at the time the study was terminated (10 weeks). Serum was separated and stored at –80° C.

Mice were examined daily for the presence of arthritis in peripheral joints. Disease was evaluated using a severity index as previously described (Wooley, *Meth. Enzymol*, 162:361–373, 1988, which is incorporated herein by reference; see, also, Wooley et al., supra, 1981). Briefly, each limb was scored as "0" (normal appearance and flexion), "1" (erythema and edema), "2" (visible joint distortion), or "3" (ankylosis detected on flexion). Paw widths were measured using constant-tension calipers.

Serum measurements for IL-1β, TNFα, IL-6 and IL-2 were obtained using the appropriate "CYTOSCREEN" mouse cytokine ELISA kit (BioSource International; Camarillo Calif.). Assays were performed according to the manufacturers' instructions. Standard curves were generated using the "SOFTMAX" computer software package (Version 2.35; Molecular Devices Services Corp.) and the levels of cytokines in the serum samples were determined by regression analysis. Student's T test and nonparametric median statistical analyses were performed using the "SPSS/PC" software package (SPSS, Inc.; Chicago Ill.).

Administration of CRA-2 resulted in a dose dependent decrease in the incidence of CIA. Specifically, 75% of control mice developed CIA, whereas only 60%, 30% or 20% of the mice receiving 3 μg, 30 μg, 300 μg CRA-2, respectively, developed CIA. In addition, a dose dependent delay in the onset of arthritis (see FIG. 1) and a reduction in the progression of disease from the inflammatory phase to the deforming phase was observed. Changes in cytokine levels from individual pretreatment samples were determined in mice that developed CIA, except that variability in the IL-2 levels between control and treated animals precluded comparisons of this cytokine. Control mice that developed CIA showed elevated IL-1 (approximately 3×) and IL-6 (approximately 2×) levels and nominally elevated TNFα levels at the time of disease onset.

Administration of CRA-2 had no significant effect on the increase in serum IL-1 levels either at the onset of CIA or at the conclusion of the study. CRA-2 caused a reduction in TNFα levels both at the onset of CIA and at the end of the study. While it appeared that TNFα levels were reduced in the group treated with 300 μg CRA-2, the result was not statistically significant. In comparison, CRA-2 caused a statistically significant, dose dependent decrease in IL-6 levels, which, at the time of onset of the disease, were below the pretreatment levels. At the end of the study (10 weeks), there was no absolute reduction in the levels of the examined cytokines in the CRA-2 treated mice as compared to the control animals.

Administration of 300 μg CRA-1, but not the lower doses, delayed the onset of CIA (see FIG. 2), but did not decrease the incidence of the disease. Although not statistically significant, the IL-1 levels in the mice treated with CRA-1 did not increase as high as the level in control mice at either the onset of disease or at the end of the study. Similarly, the levels of IL-6 were not significantly different in the control and treated animals at the onset of disease or at the end of the study. In comparison, treatment with 30 μg or 300 μg CRA-1 resulted in a significant decrease in TNFα levels at the onset of disease and at the end of the study as compared to the levels in control mice.

These results indicate that CRA-2 has a dose depending anti-arthritic effect in that it delayed the onset of arthritis and reduced the progression of the disease. The dose dependent anti-arthritic effect correlated with a dose-dependent decrease in IL-6 levels in the mice at the time of disease onset. CRA-1 (300 μg) also was effective in delaying the development of the disease, although the magnitude of the anti-arthritic effect was not as great as the corresponding decrease in TNFα levels in the treated animals.

Although the invention has been described with reference to the examples provided above, it should be understood that various modifications can be made without departing from the spirit of the invention. Accordingly, the invention is limited only by the following claims.

We claim:

1. A method for reducing the severity of rheumatoid arthritis in an individual susceptible to developing rheumatoid arthritis, comprising administering to the individual an effective dose of a cytokine regulatory agent (CRA) having the structure $X_1$—$X_2$—His—(D)Phe—Arg—(D)Trp—$X_3$, wherein $X_1$ is

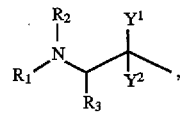

H or COCH$_3$;

H₂ is

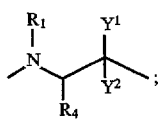

and

H₃ is

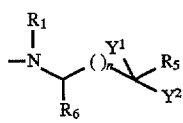

or NH₂;

wherein $Y^1$ and $Y^2$ are independently a hydrogen atom, or are taken together to form a carbonyl or thiocarbonyl;

$R_1$ is H, $COCH_3$, $C_2H_5$, $CH_2Ph$, $COPh$, $COOCH_2Ph$, $COO$-t-butyl, $CH_2CO$-(polyethylene glycol) or A;

$R_2$ is H or $COCH_3$;

$R_3$ is a linear or branched alkyl group having 1 to 6 carbon atoms;

$R_4$ is $(CH_2)_m$—$CONH_2$, $(CH_2)_m$—$CONHR_1$ or $(CH_2)_m$—$CONHA$;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula

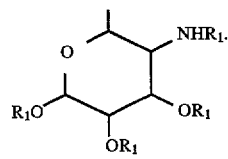

2. The method of claim 1, wherein the amino terminus of said CRA is acetylated.

3. The method of claim 1, wherein the carboxyl terminus of said CRA is amidated.

4. The method of claim 1, wherein $R_1$ is selected from the group consisting of H, $C_2H_6$ and $CH_2Ph$.

5. The method of claim 1, wherein $R_1$ and $R_2$ are each H.

6. The method of claim 1, wherein $X_1$ is selected from the group consisting of norleucine, norvaline, leucine and isoleucine.

7. The method of claim 1, wherein $R_5$ is covalently bound to $X_1$, forming a cyclic peptide.

8. The method of claim 1, wherein said CRA has the structure Ac—Nle—Gln—His—(D)Phe—Arg—(D)Trp—Gly—NH₂.

9. A method for reducing the severity of rheumatoid arthritis in an individual susceptible to developing rheumatoid arthritis, comprising administering to the individual an effective dose of a CRA having the structure X₄—His—(D)Phe—Arg—(D)Trp—X₃, wherein X₄ is

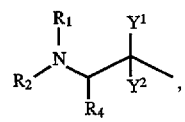

H, or COCH₃;

and

X₃ is

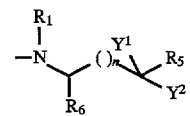

or NH₂;

wherein $Y^1$ and $Y^2$ are independently a hydrogen atom, or are taken together to form a carbonyl or thiocarbonyl;

$R_1$ is H, $COCH_2$, $C_2H_5$, $CH_2Ph$, $COPh$, $COOCH_2Ph$, $COO$-t-butyl, $CH_2CO$—(polyethylene glycol) or A;

$R_2$ is H or $COCH_3$;

$R_4$ is $(CH_2)_m$—$CONH_2$, $(CH_2)_m$—$CONHR_1$ or $(CH_2)_m$—$CONHA$;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula

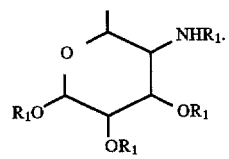

10. The method of claim 9, wherein the amino terminus of said CRA is acetylated.

11. The method of claim 9, wherein the carboxyl terminus of said CRA is amidated.

12. The method of claim 9, wherein $R_1$ is selected from the group consisting of H, $C_2H_5$ and $CH_2Ph$.

13. The method of claim 9, wherein $R_1$ and $R_2$ are each H.

14. The method of claim 9, wherein $R_5$ is covalently bound to $X_4$, forming a cyclic peptide.

15. The method of claim 9, wherein the CRA has the structure Ac—His—(D)Phe—Arg—(D)Trp—Gly—NH₂.

* * * * *

UNITED STATES PATENT AND TRADEMARK OFFICE
CERTIFICATE OF CORRECTION

PATENT NO. : 5,741,774
DATED : April 21, 1998
INVENTOR(S) : Girten et al.

Page 1 of 1

It is certified that error appears in the above-identified patent and that said Letters Patent is hereby corrected as shown below:

Column 5,
Line 36, please delete "$CH_2)_m$-$CON_2$" and replace therefor with -- $(CH_2)_m$-$CONH_2$ --.

Column 7,
Line 34, please delete "(D)Trp-$N_2$;" and replace therefor with -- (D)Trp-$NH_2$; --.

Column 13, claim 1,
Line 1, please delete "$H_2$" and replace therefor with -- $X_2$ --.
Line 10, please delete "$H_3$" and replace therefor with -- $X_3$ --.

Signed and Sealed this

Nineteenth Day of February, 2002

Attest:

Attesting Officer

JAMES E. ROGAN
*Director of the United States Patent and Trademark Office*